(12) United States Patent
Levin

(10) Patent No.: US 6,569,130 B1
(45) Date of Patent: May 27, 2003

(54) CHRONIC PERITONEAL DIALYSIS SAC

(76) Inventor: John M. Levin, 819 Chauncey Rd., Narberth, PA (US) 19072

( * ) Notice: Subject to any disclaimer, the term of this patent is extended or adjusted under 35 U.S.C. 154(b) by 76 days.

(21) Appl. No.: 09/833,288

(22) Filed: Apr. 12, 2001

(51) Int. Cl.$^7$ .............................................. A61M 31/00
(52) U.S. Cl. .................................... 604/288.01; 604/29
(58) Field of Search ................................ 604/29, 93.01, 604/204, 200, 890.1, 891.1, 892.1, 175, 174, 288.01, 288.02, 288.03, 288.04

(56) References Cited

U.S. PATENT DOCUMENTS

| | | | | |
|---|---|---|---|---|
| 3,707,967 A | * | 1/1973 | Kitrilakis et al. | 128/213 |
| 4,368,737 A | * | 1/1983 | Ash | 604/175 |
| 4,405,305 A | * | 9/1983 | Stephen et al. | 604/49 |
| 4,681,570 A | * | 7/1987 | Dalton | 604/282 |

* cited by examiner

*Primary Examiner*—Manuel Mendez
(74) *Attorney, Agent, or Firm*—Caesar, Rivise, Bernstein, Cohen & Pokotilow, Ltd.

(57) ABSTRACT

An internal peritoneal dialysis prosthesis and method employing an abdominal sac adapted to be retained in the abdominal region of a patient's body and including dialysate therein for permitting unconcentrated urine within the peritoneal region to pass through a semi-permeable membrane wall of the abdominal sac. The unconcentrated urine within the abdominal sac is directed for subsequent excretion from the patient's body via a reservoir in liquid communication with the abdominal sac. In a preferred embodiment, the abdominal sac includes a central region and lobes of semi-permeable membrane extending from the central region. The lobes are constructed to preferably extend between folds of bowel and mesentery to increase the interface area between the sac and abdomen, and maximize diffusion and ultrafiltration of urine from the mesenteric parentis and peritoneum.

20 Claims, 2 Drawing Sheets

CHRONIC PERITONEAL DIALYSIS SAC

FIELD OF THE INVENTION

This invention relates to generally to prosthesis for continuous internal peritoneal dialysis and a method of carrying out peritoneal dialysis. More specifically, this invention relates to artificial kidneys, and more specifically to artificial kidneys implantable within a person's body with the intent that the patient be free from constant dialysis and transplantation. The artificial kidneys of this invention cause the removal of fluids from the person's body. For the treatment of edema states that are refractory to treatment with diuretics the dialysate can be a selected hypertonic solution for removing excess fluids; principally water.

BACKGROUND OF THE INVENTION

The dialysis art is a highly developed one; providing a variety of teachings for dialyzing a patient. Related art teachings include hemodialysis, kidney transplantation, and introduction of a dialysate into a patient's abdomen or bloodstream.

In accordance with a related dialysis procedure (e.g., hemodialysis) for purifying blood in a patient experiencing kidney failure, the contaminated blood is directed from a blood vessel of the patient's arm through a dialyzing membrane located extracorporeally of the body, in which the blood gives up its impurities to the dialyzing fluid. The purified blood is then directed back into the patient's body through another blood vessel. A representative disclosure of a system for use in purifying arterial blood and providing a venous return is disclosed in U.S. Pat. No. 3,579,441, issued to Brown.

The dialysis art suggests the use of related peritoneal dialysis systems wherein a dialysate is introduced directly into the abdomen of the patient and functions to receive impurities from the blood at the abdominal capillaries, and then is mechanically removed from the body. Representative peritoneal dialysis systems of this type are disclosed in U.S. Pat. No. : 4,681,564 (Landreneau); U.S. Pat. No. 4,655,762 (Rogers); U.S. Pat. No. 4,586,920 (Peabody) and U.S. Pat. No. 4,437,856 (Valli).

The absorption of dialysate into the bloodstream interferes with the peritoneum dialysate's ability to do its job of pulling in fluids. Therefore, peritoneal dialysis relies physiologically on the fact that the dialysis fluid in the abdominal cavity is more viscous or thicker than blood. In other words, the dialysis fluid has a higher osmolality or chemical potential than the bloodstream. This difference in potential causes water and other molecules known to those skilled in the art to diffuse into the abdomen via the semi-permeable membranes of the peritoneum and mesenteric parietes which line the abdominal cavity.

The related art systems known to applicants suffer from one or more disadvantages. For example, a number of prior art systems require that the patient be connected, e.g., "hooked-up", to a dialysis machine. This renders the patient immobile during treatment, is expensive to administer, and subjects the patient to a high risk of infection, and even death. Patients are protein restricted, because protein yields toxic degradation products (e.g., nitrogenous wastes) largely responsible for uremia, the state of being in kidney failure. Toxic levels of potassium may also result from the treatment.

Additionally, most previous modes of dialysis have been essentially intermittent, rather than continuous; resulting in a variety of disturbances to the body's equilibrium. Patients become either over-hydrated or under-hydrated due to the intermittent process of adding and removing fluids. The systems can not maintain proper blood volume and chemical balance beyond the few hours following the treatment. The treatments sap the patient's energy and sense of well-being, making the patient look and feel chronically ill, and critically affecting the patient's lifestyle, happiness and longevity.

Typically in chronic peritoneal dialysis, the dialysate is introduced directly into the peritoneal space via a catheter and removed after it has drawn in urine. Chronic contact of the peritoneum with hypertonic dialysate solutions often creates chronic peritonitis, which is a painful, dangerous condition that interferes with the peritoneal dialysis process. In fact, it should be noted that in related peritoneal dialysis, direct contact of dialysate in the peritoneal cavity creates major problems with the chronic peritoneal dialysis procedure. Peritoneal irritation and chronic thickening caused by the dialysis leads to poor diffusion and ultra filtration. Tonicity in the peritoneal cavity increases, which draws fluid back into the cavity. Reabsorption of dialysate and unconcentrated urine interferes with the process of discarding this excessive fluid.

Moreover, dialysate that is in direct contact with the peritoneal cavity interferes with the very difference in osmotic pressure needed for the whole process of diffusion and ultra filtration. Even if the dialysate molecule is inert versus the sugar, salt or albumin used in standard dialysis, each of which causes its own special problems when reabsorbed by the lymphatic system, it creates a tremendous problem with oncotic pressure. In addition, the dialysate in the peritoneal space can cause problems in the bloodstream (e.g., hypertonic sugar, hypertonic salt, increases in nitrogenous wastes, and problems in the bloodstream including bleeding and clotting disorders, poisoning various enzyme systems, antigen-antibody reactions, D-C, etc.).

With respect to transplantation, the high cost and risks are well known. A match for the patient must be found, which may take years. If a kidney is found, and the patient is still strong enough to receive it, then there is no guarantee that the kidney will be accepted. The patient's immune system may recognize a kidney transplanted from another as foreign matter and act to combat and reject this perceived invasion. Anti-rejection medication, such as azathioprine, cyclosporine and steroids help to prevent rejection. However, anti-rejection medicines have a large number of side effects. If rejection occurs, treatment is available to possibly reverse the episode, but at the cost of more medication and side effects. With kidney transplantation, about one third of the patients do very well, about one third remain chronically ill, and about one third of the patients die within five years.

A need clearly exists for a prosthesis that is lower in cost than existing systems, that can be utilized with a minimum of risk to the patient and that provides greater freedom of movement for the patient. Therefore, it would be beneficial to provide an internal peritoneal dialysis prosthesis and method. It would also be beneficial to provide an internal peritoneal dialysis prosthesis and method which is simple in operation and requires relatively few, if any, moving parts.

SUMMARY OF THE INVENTION

One preferred embodiment of the present invention includes a prosthesis for internal peritoneal dialysis. The prosthesis comprises an abdominal sac, a subcutaneous access reservoir and a conduit. The abdominal sac is arranged to include a dialysate therein, the abdominal sac has a wall including a first semi-permeable membrane. The abdominal sac is adapted to be retained in the abdominal region of a patient's body for receiving unconcentrated urine through the first semi-permeable membrane without permitting the dialysate to exit through the wall of the abdominal sac.

The subcutaneous access reservoir is adapted to be retained in the patient's body substantially adjacent the patient's skin. The subcutaneous access reservoir is in fluid communication with the abdominal sac for delivering dialysate to the abdominal sac and removing the received unconcentrated urine from the abdominal sac. The conduit provides the fluid communication between the abdominal sac and the subcutaneous access reservoir.

In this preferred embodiment, the received unconcentrated urine exits the abdominal sac through only the conduit or the first semi-permeable membrane. The abdominal sac of this preferred prosthesis may also include a main body portion and a plurality of finger portions extending therefrom. The finger portions are arranged for placement between layers of mesentery membrane to maximize the surface area of the abdominal sac between the layers.

In another preferred embodiment of the present invention, the prosthesis for internal peritoneal dialysis includes containing means, subcutaneous accessing means and passage means. The containing means is an approach for holding a dialysate therein, the containing means has a wall including a first semi-permeable membrane. The containing means is adapted to be retained in the abdominal region of a patient's body for receiving unconcentrated urine through the first semi-permeable membrane without permitting the dialysate to exit through the wall of the containing means.

The subcutaneous accessing means is an approach for delivering dialysate to the containing means and removing the received unconcentrated urine from the containing means. The subcutaneous accessing means is adapted to be retained in the patient's body substantially adjacent the patient's skin, and has fluid communication with the containing means. The passage means is an approach for providing the fluid communication between the containing means and the subcutaneous accessing means.

In this preferred embodiment, the received unconcentrated urine exits the containing means through only the passage means or the wall of the containing means. The containing means of this preferred prosthesis may also include a main body portion and a plurality of finger portions extending therefrom. The finger portions are arranged for placement between layers of mesentery membrane to maximize the surface area of the abdominal sac between the layers.

The present invention, in another preferred embodiment includes a method for withdrawing unconcentrated urine from a patient. The method comprises depositing an abdominal sac, a subcutaneous access reservoir and a conduit in the abdominal region of a patient. The sac is adapted to receive a dialysate therein, and has a wall including a first semi-permeable membrane for receiving unconcentrated urine through the semi-permeable membrane without permitting the dialysate to exit through the semi-permeable membrane. The conduit provides fluid communication between the abdominal sac and the subcutaneous access reservoir for delivering dialysate to the abdominal sac and for removing the received unconcentrated urine from the abdominal sac. This method also includes placing the subcutaneous access reservoir substantially adjacent the patient's skin, and injecting the dialysate into the abdominal sac. The received unconcentrated urine exits the abdominal sac through only the conduit or the first semi-permeable membrane. For an abdominal sac that includes a main body portion and a plurality of finger portions extending therefrom, the method may also include the step of placing the finger portions between layers of mesentery membrane to maximize the surface area of the abdominal sac between the layers.

BRIEF DESCRIPTION OF THE DRAWINGS

The invention will be described in conjunction with the following drawings in which like reference numbers designate like elements, and wherein.

DETAILED DESCRIPTION OF THE INVENTION

Figure 1:
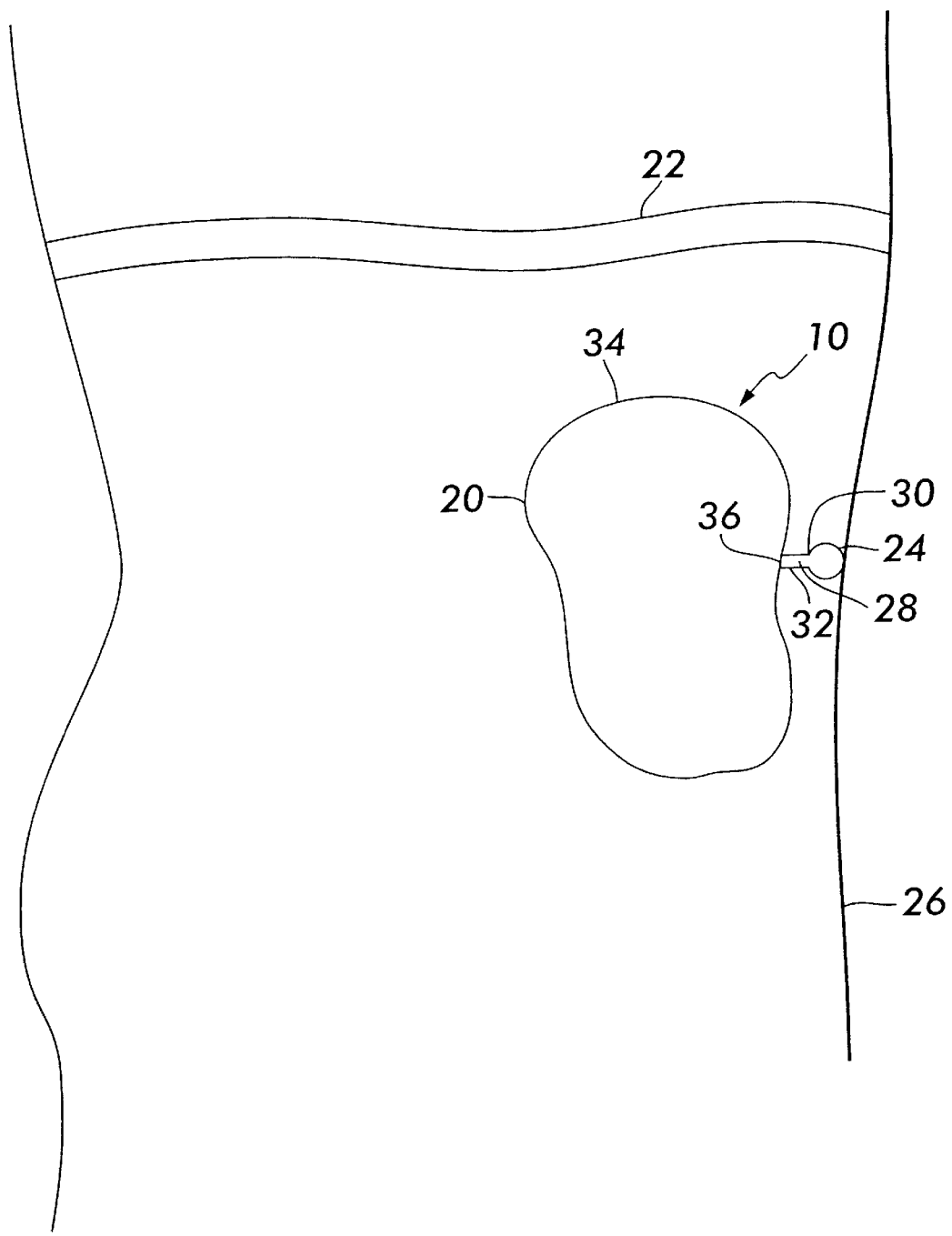
FIG. 1 is a front view of an exemplary internal peritoneal dialysis prosthesis of a preferred embodiment of the present invention showing parts thereof in section and being located in a person's body.

Referring to FIG. 1, an exemplary internal peritoneal dialysis prosthesis inserted within a patient's body is schematically illustrated at 10. The prosthesis 10 includes an abdominal sac 20 in the abdominal region of the patient below the patient's diaphragm 22, a subcutaneous access reservoir 24 substantially adjacent the patient's skin 26, and a conduit 28 providing fluid communication between the abdominal sac 20 and the subcutaneous access reservoir 24.

Still referring to FIG. 1, the abdominal sac 20 is connected to the subcutaneous access reservoir 24 through the conduit 28. The conduit 28 has a proximal end 30 and a distal end 32. The conduit 28 permits fluid (e.g., dialysate, urine) to flow between the abdominal sac 20 and the subcutaneous access reservoir 24, as will be described in greater detail below.

The abdominal sac 20 includes a wall 34 formed of a semi-permeable membrane. The outer wall 34 includes a port 36 for receiving the distal end 32 of the conduit. After the conduit 28 is in communication with the port 36, the wall 34 of the abdominal sac 20 is preferably sutured about the conduit 28 to retain the conduit 28 within the port 36.

The semi-permeable membrane has pores or apertures (holes) that provide the membrane with a porosity which precludes dialysate within the abdominal sac 20 from escaping into the peritoneal region, but still permits unconcentrated urine within the peritoneal region to enter the dialysis sac through osmotic pressure. Therefore, in this example of the preferred embodiment, the dialysate is contained within the abdominal sac 20. Because the abdominal sac 20 is required to function in an aqueous environment, it preferably is formed of a synthetic plastic material with some elastic qualities. However, the abdominal sac 12 should not be so elastic as to expand to an extent that permits the dialysate molecules or microstructures to exit from expanded pores of its wall 34.

In order to prevent the abdominal sac 20 from expanding to an extent that permits the dialysate to exit its wall 34, portions of the wall 34 may alternatively be formed of an impermeable or substantially impermeable membrane that is more elastic than the semi-permeable membrane and does not permit the dialysate to exit, even when the impermeable or substantially impermeable membrane is expanded beyond its elastic limit. Therefore, before the semi-permeable membrane expands under pressure to an extent that could permit dialysate to exit, the impermeable or substantially impermeable membrane stretches to contain the dialysate while inhibiting the dialysate from exiting therefrom. Also, the impermeable membrane could be made elastic and semi-permeable membrane inelastic.

In an exemplary environment of this invention, the dialysate exerts chemical potential to draw in unconcentrated urine (e.g., fluid wastes, electrolytes, etc.) via the adjacent peritoneum and mesenteric parieties. The dialysate can be a large inert molecule or microstructure (e.g., microspheres, such as a 50 micron polyelectrolyte or L-racemate of any giant inert molecule) which cannot exit the sac. It should be understood that, in accordance with the broadest aspects of this invention, the specific dialysate employed does not constitute a limitation on the present invention. However, the particle size of the dialysate must be such that the dialysate does not escape through the semi-permeable membrane of the abdominal sac 20 during operation of the prosthesis 10.

Ideally, the pores or apertures in the semi-permeable membrane should be about 10 microns non-expanded to about 20 microns expanded, while the dialysis molecule should have a nominal size in the range of 50 to 100 microns. Of course, these numerical values are disclosed for purposes of illustration only, and are not intended to limit the scope of the present invention.

The semi-permeable membrane can be made of any suitable synthetic plastic material, such as a Gortex-like cloth, and the dialysate can be made from a wide variety of molecules or microstructures well-known to those skilled in the art. The conduit 28 and impermeable portions of the wall 34 of the abdominal sac 20 are preferably made from silicon plastic, which is inert and does not cause peritoneal irritation.

In the preferred form of this invention, the abdominal sac 20 is positioned between the peritoneum and mesenteric parieties in the left lower quadrant of the abdomen to extract fluids (unconcentrated urine) via osmotic diffusion and ultra filtration by the same physiological principles that control regular peritoneal dialysis. The abdominal sac 20 swells with unconcentrated urine which traverses the semi-permeable membrane. As shown in FIG. 1, the dialysate does not leave the abdominal sac 20 and therefore cannot be absorbed by the lymphatic system or irritate the peritoneum. The unconcentrated urine entering the abdominal sac 20 through the semi-permeable membrane will then be directed through the conduit into the subcutaneous access reservoir for removal from the body, as described later in this application. It should be understood that preferably neither the conduit 28 nor the subcutaneous access reservoir 24 have any permeability, i.e., they are preferably impermeable so as to preclude the escape of any unconcentrated urine therefrom.

As is shown in FIG. 1, the abdominal sac 20 communicates with the subcutaneous access reservoir 24, which includes an access section closely adjacent the patient's skin 26. The subcutaneous access reservoir 24 (SAR) permits the monitoring and testing of the urine in order to determine the effectiveness of the prosthesis. The SAR 24 also permits adjustments of urine flow and urine constituents by adding or subtracting dialysate to fit each patient's needs. The dialysate can be added or withdrawn from the subcutaneous access reservoir 24, i.e., by using a syringe or tube inserted through the patient's skin into the reservoir.

In order to operate the prosthesis 10, the abdominal sac 20, conduit 28 and SAR 24 are inserted into the abdomen of the patient. Preferably the SAR 24 is positioned substantially adjacent the patient's skin 26. In this position, the SAR 24 is not visible to other people, but is easily accessible through the skin 26, preferably via a hollow needle.

The dialysate is injected into the SAR 24, and flows into the abdominal sac 20 via the conduit 28. Once in the abdominal sac 20, the dialysate exerts chemical potential to draw in unconcentrated urine from the abdomen into the sac. The abdominal sac 20 fills up and expands from the drawn in unconcentrated urine. As noted above, the dialysate does not escape through the wall 34 of the abdominal sac 20 during operation of the prosthesis 10.

The dialysate and drawn in urine are then withdrawn from the abdominal sac 20. The dialysate and urine are withdrawn by providing fluid communication between the SAR 24 and a fluid extracting device (e. g., a syringe, tube, needle). Preferably a hollow needle is inserted through the skin into the SAR 24, and a vacuum or differential pressure is created to extract the dialysate and urine from the abdominal sac 20 via the conduit 28 and SAR 24. Alternatively, the fluid extracting device could filter the drawn in urine from the dialysate and withdraw only the urine from the abdominal sac 20. However, this process may be more time consuming, and thus, more uncomfortable for the patient.

After withdrawal of the drawn in urine, dialysate may be injected into the SAR 24 as needed to replace any dialysate previously withdrawn in urine. It is understood that the amount of dialysate injected into the prosthesis 10 depends on several factors, as readily understood by a skilled artesian, such as the size and capacity of the abdominal sac 20, the amount of potential created by the dialysate, the rate that unconcentrated urine is drawn in, the length of time until the drawn in urine is removed from the prosthesis, and the comfort, safety and condition of the patient.

It is important to note that in this exemplary prosthesis of this preferred embodiment, there is no free dialysate in the peritoneal cavity; the dialysate being retained in the abdominal sac 20. It is only in such a system that it is both safe and advantageous for there to be lymphatic reabsorption. Therefore, it should be emphasized that the internal peritoneal dialysis prosthesis and method of this preferred embodiment is highly advantageous because the dialysate itself is separate at all times from the peritoneal space and from lymphatic absorption.

It also should be noted that, in a manner identical to the functioning of a normal kidney, the lower the serum osmolality (the more liquids a patient consumes) the better the peritoneal system of this invention works. In particular, the greater the differential between the osmotic pressure in the abdominal sac 20 employed in this invention and the urine, the greater the performance of the prosthesis 10.

Figure 2:
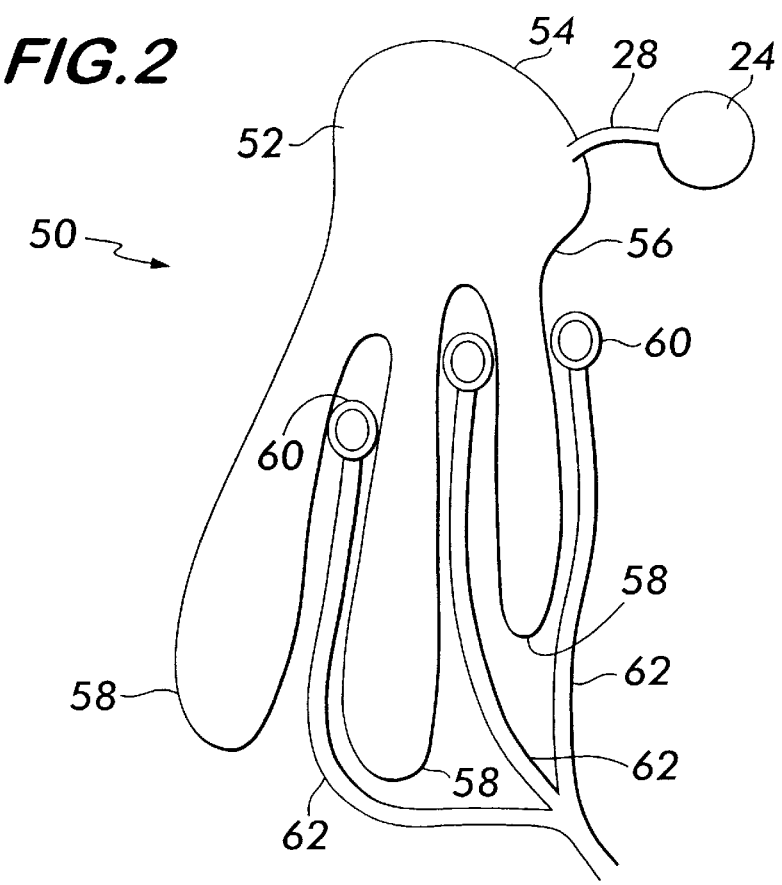
FIG. 2 is a side view of an exemplary internal peritoneal dialysis prosthesis of another preferred embodiment of the present invention showing parts thereof in section and being located in a person's body.

FIG. 2 is a side view of an exemplary internal peritoneal dialysis prosthesis 50 of another preferred embodiment of the present invention. The prosthesis 50 shown in FIG. 2 is constructed similar to the prosthesis 10 shown in FIG. 1. However, in this embodiment, the abdominal sac is formed to have a shape arranged to maximize diffusion and ultrafiltration in the mesenteric parentis and peritoneum of the patient. In order to maximize the diffusion and ultrafiltration, the abdominal sac is shaped to increase its interface area with the abdomen.

As shown in FIG. 2, the prosthesis 50 includes an abdominal sac 52 in the abdominal region of the patient, the subcutaneous access reservoir (SAR) 24 substantially adjacent the patient's skin 26, and conduit 28 providing fluid communication between the abdominal sac 52 and the SAR 24.

The abdominal sac 52 has a wall 54 generally formed of a semi-permeable membrane having a porosity which precludes the dialysate within the abdominal sac 52 from escaping into the peritoneal region, but still permits unconcentrated urine within the peritoneal region to enter the abdominal sac 52 through osmotic pressure. Because the abdominal sac 52 is required to function in an aqueous environment, it preferably is formed of a synthetic plastic material with some elastic qualities (e.g., Gortex-like cloth). However, the abdominal sac 52 should not be so elastic as to expand to an extent that permits the dialysate molecules or microstructures to exit from expanded pores of its walls.

The abdominal sac 52 may be similar to the abdominal sac 20 shown in FIG. 1. As with the abdominal sac 20 of FIG. 1, in order to prevent the abdominal sac 20 from expanding to an extent that permits the dialysate to exit the walls, portions of the wall of the abdominal sac 52 may alternatively be formed of an impermeable or substantially impermeable membrane that is more elastic than the semi-permeable membrane and does not permit the dialysate to exit, even when the impermeable or substantially impermeable membrane is expanded beyond its elastic limit. Therefore, before the semi-permeable membrane expands under pressure to an extent that could permit dialysate to exit, the impermeable or substantially impermeable membrane stretches to contain the dialysate while inhibiting the dialysate from exiting therefrom.

The abdominal sac 52 includes a central region 56 and a plurality of lobes 58 or shelves extending from the central region 56. The lobes 58 are generally formed of the semi-permeable membrane disclosed in detail above. The lobes 58 can be inserted into the abdominal region to preferably extend between folds of bowel 60 and mesentery extensions 62. Generally, the mesentery extensions include fibrous membrane communicating with the bowel that carry blood vessels to the bowel. Extending the lobes 58 between folds of bowel 60 and mesentery extensions 62 maximizes the interface area between the abdominal sac 52 and the mesentery by maximizing the surface area of the sac that is exposed to unconcentrated urine in the abdomen.

As noted above, preferably neither the conduit 28 nor the subcutaneous access reservoir 24 have any permeability, i.e., they are preferably impermeable so as to preclude the escape of any unconcentrated urine or dialysate therefrom.

The semi-permeable membrane is preferably a synthetic plastic material with some elastic qualities having a porosity which precludes dialysate from filtering through the semi-permeable membrane, but permits unconcentrated urine to filter through the material.

Figure 3:
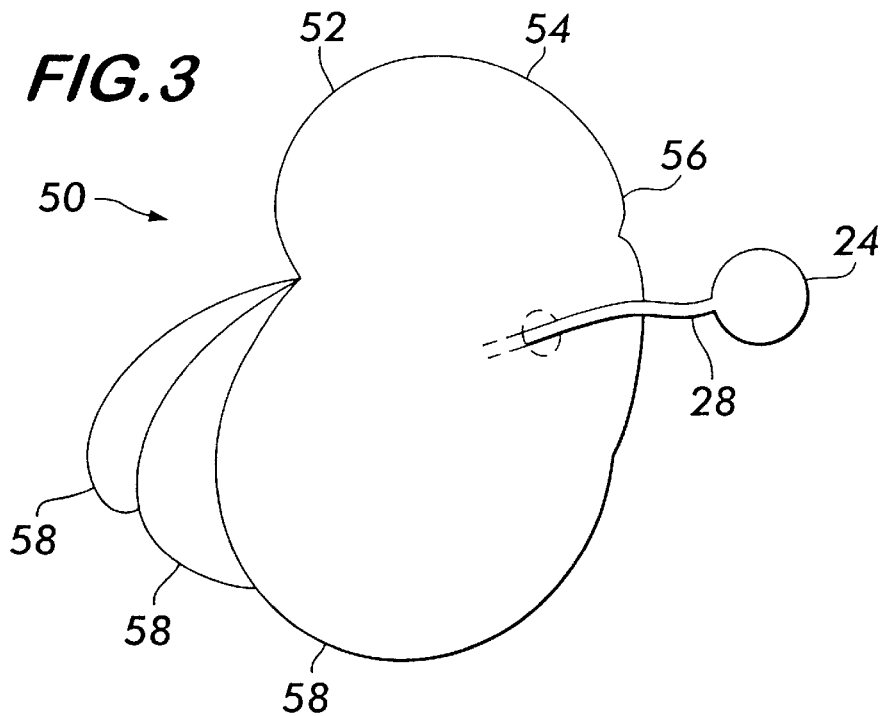
FIG. 3 is a top view of the internal peritoneal dialysis prosthesis shown in FIG. 2.

FIG. 3 is a top view of the prosthesis 50 shown in FIG. 2. Again, the prosthesis 50 includes the central region 56 and the lobes 58 extending from the central region. As illustrated in FIG. 3, the lobes 58 are shelves of wall formed of semi-permeable membrane, arranged to extend between folds of bowel and mesentery extensions. While the lobes 58 are shown generally as shelves extending from the central region 56, it is understood that the lobes 58 can be formed in any shape that increases surface and interface area between the lobes and their environment. For example, the lobes 58 could be shaped as fingers extending from the central region for insertion between bowel and mesentery folds in the abdomen.

Although the conduit is illustrated in the exemplary embodiments shown in FIGS. 1–3 as being a single separate conduit, it should be understood that, in an alternative construction, the conduit is separated into two conduits interconnected together. This construction is preferred when it is desirable to insert dialysate into the abdominal sac via one conduit, and to extract drawn in urine via a second conduit. This construction is also preferred when it is desirable to extract only the drawn in unconcentrated urine from the abdominal sac while leaving the dialysate in the sac. A filter (e.g., semi-permeable membrane) located between the abdominal sac and SAR would provide the benefit of separating the urine from the dialysate, so that only the urine is withdrawn from the prosthesis.

It should be apparent from the aforementioned description and attached drawings that the concept of the present application may be readily applied to a variety of preferred embodiments, including those disclosed herein. For example, the SARs may be attached to the abdominal sac via respective conduits. In this construction, one SAR may be used to inject the dialysate into the abdominal sac and the other SAR may be used to extract at least the urine from the sac. As another example of a preferred embodiment, the conduit 28 may comprise or be divided into several branches for extending into the abdominal sac 20, and in particular into the lobes 58, to provide improved mixing and flow of the fluids.

Without further elaboration the foregoing will so fully illustrate my invention that others may, by applying current or future knowledge, readily adapt the same for use under various conditions of service.

What I claim as the invention is:

1. A prosthesis for internal peritoneal dialysis, comprising:
    an abdominal sac being arranged to include a dialysate therein, said abdominal sac having a wall including a first semi-permeable membrane, said abdominal sac being adapted to be retained in the abdominal region of a patient's body for receiving unconcentrated urine through said first semi-permeable membrane without permitting the dialysate to exit through said wall of said abdominal sac;
    a subcutaneous access reservoir being adapted to be retained in the patient's body substantially adjacent the patient's skin, the subcutaneous access reservoir in fluid communication with the abdominal sac for delivering dialysate to said abdominal sac and removing the received unconcentrated urine from said abdominal sac; and
    a conduit providing the fluid communication between said abdominal sac and said subcutaneous access reservoir, the received unconcentrated urine exiting said abdominal sac through only said conduit or said first semi-permeable membrane.

2. The prosthesis of claim 1, wherein the conduit includes a first conduit section communicating the dialysis to said abdominal sac and a second conduit section communicating the received unconcentrated urine to said subcutaneous access reservoir.

3. The prosthesis of claim 1, wherein said conduit includes a second semi-permeable membrane having a porosity which precludes the dialysate from exiting.

4. The prosthesis of claim 1, said abdominal sac having a main body portion and a plurality of lobe portions extending therefrom, said lobe portions arranged for placement between layers of mesentery membrane to maximize the surface area of said abdominal sac between the layers.

5. The prosthesis of claim 4, said lobe portions arranged for placement between layers of the patient's mesentery.

6. The prosthesis of claim 1, wherein said dialysis is more viscous than the unconcentrated urine.

7. A prosthesis for internal peritoneal dialysis, comprising:

containing means for holding a dialysate therein, said containing means having a wall including a first semi-permeable membrane, said containing means being adapted to be retained in the abdominal region of a patient's body for receiving unconcentrated urine through said first semi-permeable membrane without permitting the dialysate to exit through said wall of said containing means;

subcutaneous accessing means for delivering dialysate to said containing means and removing the received unconcentrated urine from said containing means, said subcutaneous accessing means being adapted to be retained in the patient's body substantially adjacent the patient's skin, said subcutaneous accessing means for having fluid communication with the containing means; and passage means for providing the fluid communication between said containing means and said subcutaneous accessing means, the received unconcentrated urine exiting said containing means through only said passage means or said wall of said containing means.

8. The prosthesis of claim 7, wherein said passage means includes a first conduit section for communicating the dialysis to said containing means and a second conduit section for communicating the received unconcentrated urine to said subcutaneous accessing means.

9. The prosthesis of claim 7, wherein said passage means includes a second semi-permeable membrane having a porosity which precludes the dialysate from exiting.

10. The prosthesis of claim 7, said containing means having a main body portion and a plurality of lobe portions extending therefrom, said lobe portions arranged for placement between layers of mesentery membrane to maximize the surface area of said abdominal sac between the layers.

11. The prosthesis of claim 10, said lobe portions arranged for placement between layers of the patient's mesentery.

12. The prosthesis of claim 7, wherein said dialysis is more viscous than the unconcentrated urine.

13. The prosthesis of claim 7, further comprising:

depositing means for injecting the dialysate into said subcutaneous accessing means; and withdrawing means for removing the received unconcentrated urine from said subcutaneous accessing means.

14. A method for withdrawing unconcentrated urine from a patient, comprising:

depositing an abdominal sac, a subcutaneous access reservoir and a conduit in the abdominal region of a patient, the sac being adapted to receive a dialysate therein, the abdominal sac having a wall including a first semi-permeable membrane for receiving unconcentrated urine through the semi-permeable membrane without permitting the dialysate to exit through the semi-permeable membrane, the conduit providing fluid communication between the abdominal sac and the subcutaneous access reservoir, the received unconcentrated urine exiting the abdominal sac through only the conduit or the first semi-permeable membrane;

placing the subcutaneous access reservoir substantially adjacent the patient's skin, the subcutaneous access reservoir in fluid communication with the abdominal sac for delivering dialysate to the abdominal sac and removing the received unconcentrated urine from the abdominal sac; and injecting the dialysate into the abdominal sac.

15. The method of claim 14, wherein the conduit includes a first conduit section communicating the dialysis to the abdominal sac and a second conduit section communicating the received unconcentrated urine to the subcutaneous access reservoir.

16. The method of claim 14, wherein the conduit includes a second semi-permeable membrane having a porosity which precludes the dialysate from exiting.

17. The method of claim 14, the abdominal sac having a main body portion and a plurality of lobe portions extending therefrom, and further comprising placing the lobe portions between layers of mesentery membrane to maximize the surface area of the abdominal sac between the layers.

18. The method of claim 17, the lobe portions arranged for placement between layers of the patient's mesentery.

19. The method of claim 14, wherein the dialysis is more viscous than the unconcentrated urine.

20. The method of claim 14, further comprising withdrawing the received unconcentrated urine from the subcutaneous access reservoir.

* * * * *